US012283377B2

(12) United States Patent
Hong

(10) Patent No.: US 12,283,377 B2
(45) Date of Patent: *Apr. 22, 2025

(54) ATHLETE MANAGEMENT APPARATUS FOR MANAGING STATE OF ATHLETE IN CONJUNCTION WITH PROTECTOR WORN BY ATHLETE, ATHLETE MANAGEMENT SYSTEM, AND ATHLETE MANAGEMENT METHOD USING SAME

(71) Applicant: Sun Ki Hong, Seoul (KR)

(72) Inventor: Sun Ki Hong, Seoul (KR)

( * ) Notice: Subject to any disclaimer, the term of this patent is extended or adjusted under 35 U.S.C. 154(b) by 283 days.

This patent is subject to a terminal disclaimer.

(21) Appl. No.: 17/948,221

(22) Filed: Sep. 19, 2022

(65) Prior Publication Data
US 2023/0028016 A1 Jan. 26, 2023

Related U.S. Application Data

(62) Division of application No. 15/743,544, filed as application No. PCT/KR2016/006764 on Jun. 24, 2016, now Pat. No. 11,450,429.

(30) Foreign Application Priority Data

Jul. 11, 2015 (KR) .................. 10-2015-0098721
Jun. 23, 2016 (KR) .................. 10-2016-0078860

(51) Int. Cl.
G16H 40/67 (2018.01)
A61B 5/00 (2006.01)
A61B 5/0205 (2006.01)
A61B 5/026 (2006.01)
A61B 5/11 (2006.01)
A61B 5/145 (2006.01)
A63B 24/00 (2006.01)
A63B 71/12 (2006.01)
G16H 20/40 (2018.01)
A61B 5/021 (2006.01)
A61B 5/024 (2006.01)
A61B 5/08 (2006.01)
A63B 71/00 (2006.01)
A63B 71/06 (2006.01)

(52) U.S. Cl.
CPC ............ *G16H 40/67* (2018.01); *A61B 5/002* (2013.01); *A61B 5/02055* (2013.01); *A61B 5/026* (2013.01); *A61B 5/0261* (2013.01); *A61B 5/1118* (2013.01); *A61B 5/1128* (2013.01); *A61B 5/14546* (2013.01); *A61B 5/4824* (2013.01); *A61B 5/4866* (2013.01); *A61B 5/6804* (2013.01); *A61B 5/746* (2013.01); *A63B 24/0062* (2013.01); *A63B 71/1225* (2013.01); *G16H 20/40* (2018.01); *A61B 5/021* (2013.01); *A61B 5/024* (2013.01); *A61B 5/08* (2013.01); *A61B 2503/10* (2013.01); *A61B 2560/0247* (2013.01); *A61B 2560/0252* (2013.01); *A63B 71/0054* (2013.01); *A63B 71/0622* (2013.01); *A63B 2071/0625* (2013.01); *A63B 2071/0655* (2013.01); *A63B 71/12* (2013.01); *A63B 2071/1258* (2013.01); *A63B 2220/20* (2013.01); *A63B 2220/30* (2013.01); *A63B 2220/62* (2013.01); *A63B 2220/72* (2013.01); *A63B 2220/73* (2013.01); *A63B 2220/75* (2013.01); *A63B 2220/76* (2013.01); *A63B 2220/78* (2013.01); *A63B 2220/805* (2013.01); *A63B 2220/807* (2013.01); *A63B 2220/836* (2013.01); *A63B 2225/50* (2013.01); *A63B 2230/045* (2013.01); *A63B 2230/062* (2013.01); *A63B 2230/305* (2013.01); *A63B 2230/405* (2013.01); *A63B 2230/438* (2013.01); *A63B 2230/505* (2013.01); *A63B 2230/605* (2013.01)

(58) Field of Classification Search
CPC ........ G16H 40/67; G16H 20/40; A61B 5/002; A61B 5/02055; A61B 5/026; A61B 5/0261; A61B 5/81118; A61B 5/1128; A61B 5/14546; A61B 5/4824; A61B 5/4866; A61B 5/6804; A61B 5/746; A63B 24/0062; A63B 71/1255

See application file for complete search history.

(56) References Cited

U.S. PATENT DOCUMENTS

2009/0131165 A1    5/2009  Buchner et al.
2012/0081531 A1    4/2012  DeAngelis et al.
2013/0296741 A1   11/2013  Wiggin et al.
2014/0159922 A1    6/2014  Maliszewski

FOREIGN PATENT DOCUMENTS

| CN | 101778653 A | 7/2010 |
| JP | 06-319843 A | 11/1994 |
| JP | 2009-297057 A | 12/2009 |
| JP | 2013-215426 A | 10/2013 |
| KR | 10-2010-0032273 A | 3/2010 |
| KR | 10-2011-0115880 A | 10/2011 |

(Continued)

Primary Examiner — Jerry Lin
(74) Attorney, Agent, or Firm — Bridgeway IP Law Group, PLLC; Sang Ho Lee; Hyun Woo Shin

(57) ABSTRACT

Provided is an apparatus for managing a player with a guard including a sensor sensing a vital information of a player to calculate an injury risk of the player to thereby manage a condition of the player, the apparatus including: a communication unit receiving the vital information from the guard and transmitting the injury risk to the guard; a memory storing a program calculating the injury risk to manage the condition of the player; and a processor connected to the communication unit and the memory to execute an operation implemented by the program, in which the program may include instructions using the vital information and pre-stored vital recovering ability data of the player to calculate the injury risk of the player.

8 Claims, 6 Drawing Sheets

(56) References Cited

FOREIGN PATENT DOCUMENTS

| | | |
|---|---|---|
| KR | 10-1337821 B1 | 12/2013 |
| KR | 10-2015-0077684 A | 7/2015 |
| WO | 2012/100053 A1 | 7/2012 |

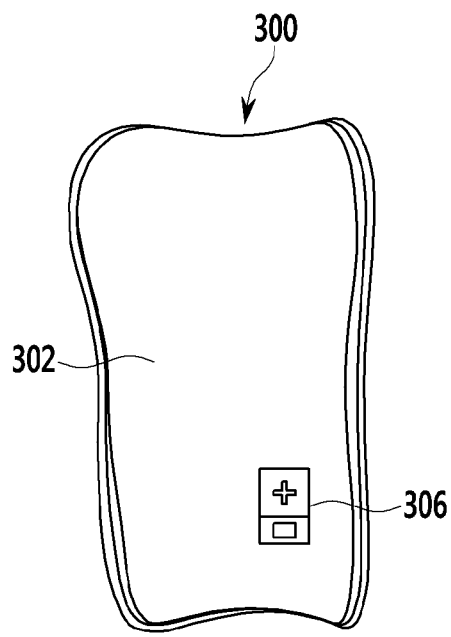
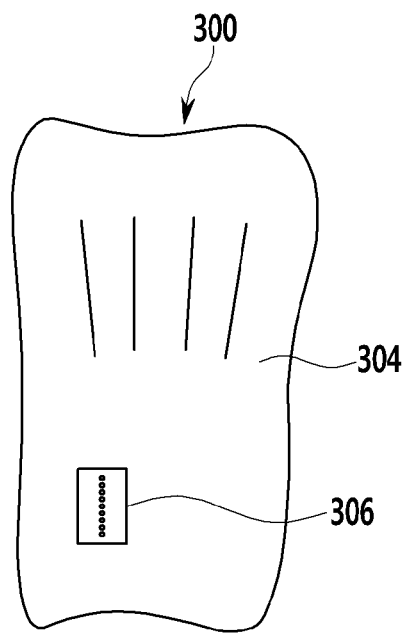
FIG. 3A  FIG. 3B
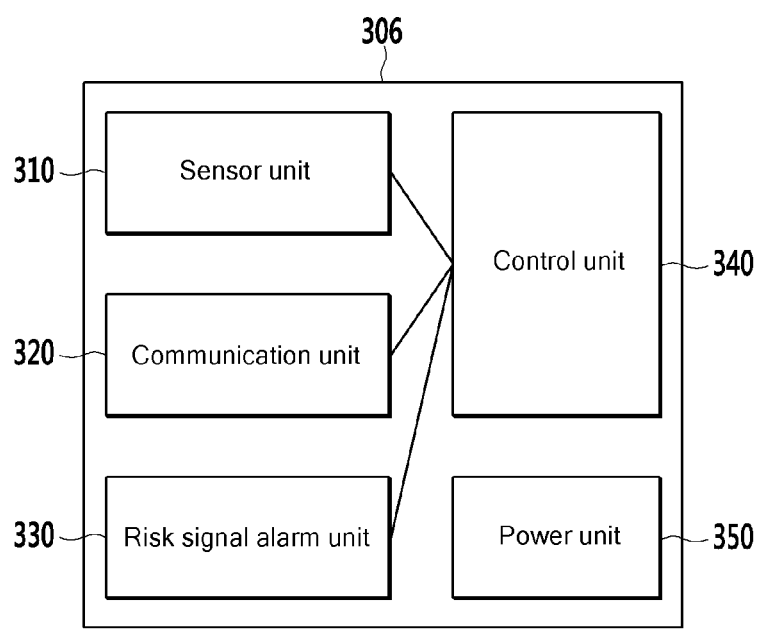
FIG. 4

ATHLETE MANAGEMENT APPARATUS FOR MANAGING STATE OF ATHLETE IN CONJUNCTION WITH PROTECTOR WORN BY ATHLETE, ATHLETE MANAGEMENT SYSTEM, AND ATHLETE MANAGEMENT METHOD USING SAME

CROSS-REFERENCE TO RELATED APPLICATIONS

The instant application is divisional of U.S. application Ser. No. 15/743,544 (filed on Jan. 10, 2018), which is a national-stage entry under 35 USC 371 of international application No. PCT/KR2016/006764 (filed on Jun. 24, 2016), and claims priority to Korean patent application Nos. 10-2015-0098721 (filed on Jul. 11, 2015) and 10-2016-0078860 (filed on Jun. 23, 2016) the entire disclosures of which are hereby incorporated by reference.

FIELD OF THE INVENTION

The present invention relates to an apparatus, a system, and a method for monitoring a body condition of a player with a guard including a sensor sensing vital information of the player and managing the player based on the monitored result.

DESCRIPTION OF THE RELATED ART

Sports players get body parts such as a thigh, a waist, a neck, a head, an arm, a hand, and a crotch injured during sports events, and therefore has aftereffects. Further, ligaments and nerves of a foot, a knee, an ankle, a waist, a neck, an arm, and a hand or internal organs are exposed to a danger.

Most of the injuries may be caused due to a physical contact among players. However, notwithstanding that there is no peculiar physical contact, an abnormal phenomenon of inner parts of a body due to an immoderate game and a training game of players is not sensed on the basis of a pressure to inner and outer parts of a body, and therefore players may die or become unconscious. When a game is in full swing, players have the maximum stress and tension and reach a physically unbearable condition, and therefore have degraded self-regulation ability, such that they may easily forget their own risk situations. As a result, players may be suddenly collapse during a game to be a vegetable of unconsciousness and even die.

Players themselves need to regulate physical danger or change of players who are in athletics or a couch and a medical staff need to manage players. However, as long as players regulate their own physical problems for themselves and as a result the physical problems of players do not alarm anybody, and therefore players who participate in a real game may not receive help from anybody.

Therefore, to cope with a change in a living body of players due to extreme conditions of competitive sports and to take a measure before players are injured during the sports events, it is very important to previously predict dangerous situations of players in real time on the basis of vital information of players who participate in a game and cope with the dangerous situations in real time. Accordingly, a technology of alarming a wearer of risk situations on an image, voice, and vibration, respectively, in real time so as to acquire vital information of players in taekwondo that is a violent marital art, players in soccer, football, baseball, rugby, formula one, ice hockey, basketball, volleyball, handball, golf, tennis, swimming, and cycle that are team sport games, a solder, a climber, a scuba diver, and players in a E sport game in real time and identify the acquired vital information to thereby prevent an injury to players and automatically analyzing and supporting a current condition of players using analysis algorithm to monitor the current condition of players in real time is urgently required.

SUMMARY OF THE INVENTION

The present invention has been made in an effort to provide a system for operating a game capable of monitoring a vital and exercise condition of players participating in a sport game under extreme conditions to analyze dangerous situations of players to thereby help regulate players' pace or change players, thereby preventing players from being injured in advance to smoothly operate a game.

An exemplary embodiment of the present invention provides an apparatus for managing a player with a guard including a sensor sensing vital information of a player and an operation and activity depending on a position of the player to calculate a warning sign and an injury risk of the player to thereby manage a condition of the player. The apparatus includes a communication unit receiving the vital information from the guard and transmitting the warning sign and the injury risk to the guard; a memory storing a program calculating the warning sign and the injury risk to manage the condition of the player; and a processor connected to the communication unit and the memory to execute an operation implemented by the program. The program may include instructions using the vital information and the pre-stored vital recovering ability data of the player to calculate the warning sign and the injury risk of the player.

The vital information may include at least any one of a blood flow, a heart rate, electrocardiogram, electromyogram, body temperature, lactic acid, sweat, in vitro secretion, respiration, oxygen saturation, moisture, in vivo nutrient, ligament elasticity, nerve reaction, and pain information and includes an activity distance, activity time, and a position of an activity operation and the program may include instructions using a variation of the vital information and the vital recovering ability data to calculate the injury risk of the player.

The communication unit may receive activity information of the player including at least one of an activity distance, activity time, an activity operation, and activity strength of the player from the guard and the program may include instructions using a variation of the vital information, the activity information of the player, and the vital recovering ability data to calculate the injury risk of the player.

The communication unit may receive stadium environment information including at least one of humidity, temperature, a wind volume, a wind direction, altitude, latitude, geological features, a ground, and grass of the stadium, that is, an inclined ball rebound, a vertical ball rebound, a ball rolling distance and speed, a size of grass, a moisture state of grass, a position, rotation, strength, an elastic force, a pressure, and a gravitational acceleration of a ball, spinning of the ball, a speed of the player and the ball, a bound, a straight, and a ground from an external terminal and the program may include instructions integrating the vital information, the vital recovering ability data of the player, and the stadium environment information to calculate the injury risk of the player.

The communication unit may receive a game image from a photographing unit positioned within a stadium and the program may calculate activity information of the player including at least one of an activity distance, activity time, an activity operation, and activity strength of the player from the game image and include instructions using a variation of the vital information, the activity information of the player, and the vital recovering ability data to calculate the injury risk of the player.

The guard may include a sensor unit sensing the vital information of the player; a communication unit transmitting the vital information and receiving the injury risk from the apparatus for managing a player; and a risk signal alarm unit for alarming the warning sign and the injury risk.

Another embodiment of the present invention provides a guard with an apparatus for managing a player using vital information of the player to calculate an injury risk of the player to alarm the player of the injury risk. The guard may include a sensor unit including at least one of a piezoelectric sensor for measuring blood pressure information of the player, a photo sensor for measuring blood flow information, an electrocardiogram sensor, a temperature sensor for measuring body temperature, lactic acid, sweat, in vitro secretion, respiration, oxygen saturation, and moisture information, and a bio sensor for sensing at least one vital information of in vivo nutrient information, moisture content information, muscle information, nerve information, ligament information, and pain information; a communication unit transmitting the vital information sensed by the sensor unit to the apparatus for managing a player and receiving the injury risk from the apparatus for managing a player; and a risk signal alarm unit including at least one of a display unit for alarming the injury risk to the outside and a vibration unit for alarming the player of the injury risk.

The sensor unit may include a plurality of sensor modules arranged in an array form and the guard may further include a control unit collecting and filtering the respective vital information sensed by the plurality of sensor modules and converting the collected and filtered vital information into a signal having a form transmittable through the communication unit.

Yet another embodiment of the present invention provides a method for managing a player with a guard including a sensor sensing a vital information of the player to allow an apparatus for managing a player to calculate an injury risk of the player to thereby manage a condition of the player, the method including receiving the vital information from the guard; calculating the injury risk using pre-stored vital recovering ability data and the vital information; and transmitting the injury risk to the guard.

The vital information may include at least any one of a blood flow, a heart rate, electrocardiogram, electromyogram, body temperature, lactic acid, sweat, in vitro secretion, respiration, oxygen saturation, moisture, in vivo nutrient, ligament elasticity, nerve reaction, and pain information.

The method may further include receiving activity information of the player including at least one of an activity distance, activity time, an activity operation, and activity strength of the player from the guard, in which in the calculating of the injury risk, the injury risk of the player may be calculated using a variation of the vital information, the activity information of the player, and the vital recovering ability data.

The method may further include receiving stadium environment information including at least any one of humidity, temperature, a wind volume, a wind direction, altitude, and geological features of a stadium, a grass state of the stadium, position information of players, and a position and a motion of a ball from an external terminal, in which in the calculating of the injury risk, the injury risk of the player may be calculated by integrating the vital information, the pre-stored vital recovering ability data of the player, and the stadium environment information.

The method may further include receiving a game image from a photographing unit positioned within a stadium, and calculating activity information of the player including at least one of an activity distance, activity time, an activity operation, and activity strength of the player from the image, in which in the calculating of the injury risk, the injury risk of the player may be calculated using a variation of the vital information, the activity information of the player, and the vital recovering ability data.

The method may further include transmitting the injury risk to a terminal carried by a coach or a medical staff monitoring the player.

Still another embodiment of the present invention provides a system for managing a player to manage a condition of the player including a guard that the player wears; and an apparatus for managing a player calculating an injury risk of the player, in which the guard may include a sensor attached to a player's body to sense vital information of the player. The apparatus for managing a player may include a vital recovering ability data storage unit storing vital recovering ability data of the player; a vital information acquisition unit receiving the vital information of the player from the guard; and an injury risk extraction unit using the vital information and the vital recovering ability data to extract the injury risk of the player.

The apparatus for managing a player may further include an environment information acquisition unit receiving environment information that affects a physical or mental condition of the player from at least one external terminal. The injury risk extraction unit may extract the injury risk of the player using the vital information, the environment information, and the vital recovering ability data.

The apparatus for managing a player may further include an activity information acquisition unit acquiring activity information including at least one of activity time, an activity distance, and activity mass of the player, and the injury risk extraction unit may extract the injury risk of the player using the vital information, the activity information, the environment information, and the vital recovering ability data.

The activity information acquisition unit may acquire the activity information from the sensor or receive a game image from a photographing unit disposed inside or outside a stadium to photograph a game scene of the player and sense a position change of the player from the game image to extract the activity information of players.

The apparatus for managing a player may further include a communication module transmitting the injury risk to the guard or a terminal carried by a coach or a medical staff monitoring the player.

Advantageous Effects

The apparatus, system, and method for managing a state player with a guard worn at a player according to an exemplary embodiment of the present invention may analyze the risk situations of players and alarm the players of the analyzed result to make the players regulate their pace for themselves, thereby predicting and preventing the injury to the players or the emergency accident.

The apparatus, system, and method for managing a state player with a guard worn at a player according to an exemplary embodiment of the present invention may integrate the vital information that are acquired from the shank guard that the players wear, the exercise environment (altitude, humidity, temperature), and the vital activity data (maximum value and minimum value of the vital information of each player) of players, thereby accurately analyzing and alarming the risk situation of players.

The guard worn at a player according to an exemplary embodiment of the present invention may stably adhere and may be fixed to the skin (epidermis) of the body without violating the equipment wearing regulations unlike a sneaker, a soccer shoe, a uniform, and a sock that are the wearing equipment of players for each sport event to easily acquire the vital information and may be worn at the risk parts to be injured and the parts such as an artery, a vein, a nerve, and a ligament to be optimized to sense the vital information of players, thereby protecting players from being injured.

BRIEF DESCRIPTION OF THE DRAWINGS

FIG. 3A is a rear view of a guard in the system for managing a player according to the exemplary embodiment of the present invention and FIG. 3B is a front view of a guard in the system for managing a player according to the exemplary embodiment of the present invention.

FIG. 4 is a diagram illustrating a configuration of the guard in the system for managing a player according to the exemplary embodiment of the present invention.

DETAILED DESCRIPTION OF THE EMBODIMENTS

Figure 1:
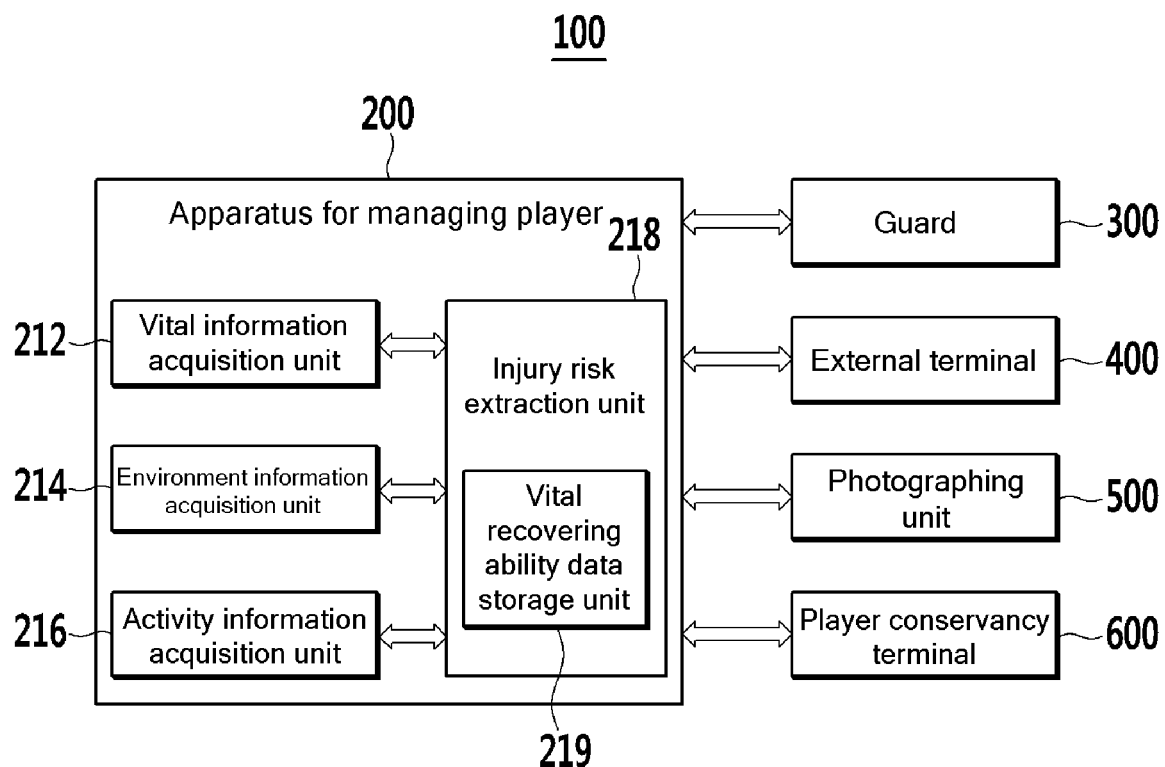
FIG. 1 is a diagram illustrating a configuration of a system for managing a player according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. In order to clearly describe the present invention, portions that are not connected with the description will be omitted. Like reference numerals designate like elements throughout the specification. In addition, the detailed description of the widely known technologies will be omitted.

Therefore, since exemplary embodiments stated in the present specification and configurations shown in the accompanying drawings are only exemplary embodiments of the present invention and do not represent the spirit of the present invention, it is to be understood that various equivalents and modifications that may replace exemplary embodiments stated in the present specification and configurations shown in the accompanying drawings at a point in time at which the present invention is filed.

Hereinafter, an apparatus, a system, and a method for managing a player with a guard worn at a player according to an exemplary embodiment of the present invention will be described.

FIG. 1 is a diagram illustrating a configuration of a system for managing a player according to an exemplary embodiment of the present invention.

Referring to FIG. 1, a system 100 for managing a player according to an exemplary embodiment of the present invention includes a guard 300 worn at a player and an apparatus 200 for managing a player with the guard 300. The system 100 for managing a player may further include an external terminal 400 that may transmit environment information of a stadium to the apparatus 200 for managing a player, a photographing unit 500 photographing a game content of a player and transmitting the photographed game image to the apparatus 200 for managing a player, and a player conservancy terminal 600 carried by a player conservancy.

The guard 300 protects an injured part and relieves a pain of a player due to an external shock while a player is in athletics and is worn while adhering to a skin to protect a body. Here, the inside of the guard 300 adheres to a skin (epidermis and dermis) to easily sense vital information of a player and the guard 300 transmits the sensed vital information to the apparatus 200 for managing a player.

The vital information means information for understanding a body condition of a player wearing the guard 300 and may include at least one of, for example, a blood pressure, a blood flow, a heart rate, electrocardiogram, body temperature, an in vivo nutrient, a total body fluid, a muscle contraction, lactic acid, a nerve, and a ligament.

The apparatus 200 for managing a player according to the exemplary embodiment of the present invention may include a vital information acquisition unit 212, an environment information acquisition unit 214, an activity information acquisition unit 216, and an injury risk extraction unit 218.

Generally, players run 3 to 11 m per second that is activity per high-intensive exercise time. If it is assumed that players run 6 m per second, they run about 21,600 m for 60 minutes and 43,200 m for 120 minutes. Although the heart rate may be different according to an age and a sex of a player, if the intensity is continued for a reference time, players have a heart rate of 220−age=maximum heart rate of 150 to 213. Players do high-intensive exercise activity and have a predetermined recovering time to recover a normal heart rate and then needs to do next activity. When a body is not normally recovered, that is, when players continuously do exercise activity without recovering time, recovering ability may significantly deteriorate or fatigability may be increased, such that players may be highly likely to be injured. Further, although extreme fatigability, a slight ache, an increase in perspiration, nausea, dizziness, shortness of breath, sleeplessness, and anxiety that are a warning sign of a heart attack and an injury may be different according to an age and a sex, there is a need to monitor the warning sign of the heart attack and the injury risk in advance to take a prevention and a measure according to a player condition.

Time when the player condition is normally recovered may be different for each player and a recovering speed may be fast or slow depending on even environmental elements in which a game is performed. The apparatus 200 for managing a player according to the exemplary embodiment of the present invention may use pre-stored vital recovering ability data of a user and a stadium and external environment information that may affect a recovering speed of a player, that is, surface hardness of grass, ground, moisture, a gravitational acceleration of a ball, a fan, noise, temperature, altitude, wind, and vital information and activity information of a player to monitor a change in a player condition, thereby acquiring an injury risk and alarming a player and a player conservancy of the acquired injury risk.

The vital information acquisition unit 212 receives vital information for understanding a player condition from the guard 300.

The environment information acquisition unit 214 receives environment information from at least one external terminal.

The environment information means information which may affect a physical or mental condition of a player. For example, the environment information may include at least one of weather information such as humidity, temperature, a wind volume, a wind direction, and noise in a stadium and stadium information such as altitude, geological features, a grass state of a playground, an air pressure of a ball, and a repulsive force of a ball.

The activity information acquisition unit 216 may acquire activity information such as activity time, an activity distance, and activity mass, etc. of a player from the guard 300 or use the game image information received from the photographing unit 500 to sense a change in position of a player from the received game image to thereby calculate a quantity of motion of players or monitor players' motions, thereby extracting the activity information of players.

The photographing unit 500 may be disposed at a goalpost, a corner flag, and a line in a stadium or outside a stadium to relay a game to photograph a game image for monitoring a position of a player as various angles.

The injury risk extraction unit 218 uses the vital information of a player received by the vital information acquisition unit 212, the environment information received by the environment information acquisition unit 214 that may affect a player, and the activity information of a player acquired by the activity information acquisition unit 216 and uses the vital recovering ability data stored in the vital recovering ability data storage unit 219 to extract the injury risk of a player. The vital recovering ability data may include at least one of data that may be generally applied according to a sex and an age of a player and an athletic event of a player and personal data that are measured during a game history and training that is already done by each player and individually accumulated.

Further, the apparatus 200 for managing a player transmits the calculated risk of injury to the guard 300 that a player wears to allow a player to control his/her own condition for himself/herself or transmits the calculated risk of injury to the player conservancy terminal 600 carried by at least one of a supervisor, a medical staff, a judge, and a coaching staff monitoring a player state and managing a game to smoothly operate the game.

That is, the system 100 for managing a player according to the exemplary embodiment of the present invention integrates the vital information of a player received from the guard 300, the environment information received from at least one external terminal 400, and the activity information of a player extracted from the game image received from the photographing unit 500 to analyze and understand a current body condition and a physical strength condition of a player. Further, the degree of injury risk is calculated on the basis of the pre-stored vital recovering ability data of players such as the past game information, training information, and injury information. The degree of injury risk is the degree that the injury risk of a player is expected or a player's health or life is in danger if a player continues a game.

According to the exemplary embodiment of the present invention, the injury risk extraction unit 218 may integrate vital analysis data, in vivo nutrient content data, environmental element analysis data, operation analysis data, and recoding data of a player to calculate the injury risk of a player in three phases of a normal phase, a warning phase, and a risk phase.

In this case, the vital analysis data may include at least one of an age of a player, a moving distance per hour, a heart rate, a recovering speed, oxygen saturation, a respiration volume, a blood pressure, lactic acid, a discharged amount of sweat, body temperature, in vitro secretion, and pain information as shown in the following Table 1.

TABLE 1

| Age (seven years old) | Distance | Heart rate | Recovery | Oxygen Saturation | Breathing | Blood Pressure (Contraction) | Blood Pressure (Relaxation) | Lactic Acid | Sweat | Body temperature |
| --- | --- | --- | --- | --- | --- | --- | --- | --- | --- | --- |
| Optimal Zone | 270 | 170 | 127.5 | 100 | 30 | 110 | 70 | 20 | 7 | 37.5 |
| Risk Zone | 270 | 213 | 202.3 | 75 | 10 | 70 | 50 | 150 | 10 | 35.5 |

A method for calculating vital analysis data is as follows.

A maximum heart rate may be calculated as the following Equation 1.

$$\text{Maximum heart rate (Max HR)} = 220 - \text{age} \quad \text{[Equation 1]}$$

A target heart rate may be calculated as the following Equation 2.

$$\text{Target heart rate} = \text{maximum heart rate} - 65\text{-}85\% \quad \text{[Equation 2]}$$

Calorie consumption per 1 minute may be calculated as the following Equation 3 or 4.

$$\text{Calorie consumption per 1 minute (kcal/min)} = 0.00094 \times \text{heart rate} + 0.1346 \times \text{body mass} - 7.37418 \quad \text{[Equation 3]}$$

$$\text{Calorie consumption per 1 minute (kcal/min)} = \text{METs} \times 3.5 \text{ (constant)} \times \text{body weight}/200 \text{ (constant)} \quad \text{[Equation 4]}$$

A maximum oxygen uptake may be calculated as the following Equation 5.

$$\text{Maximum oxygen uptake (VO2max) [ml/kg/min]} = \text{Mets} \times 3.5 \quad \text{[Equation 5]}$$

An anaerobic threshold (AT) may be calculated as the following Equation 6.

$$\text{Anaerobic threshold} = 0.7 \text{ (Max HR} - \text{Rest HR)} + \text{Rest HR} \quad \text{[Equation 6]}$$

In the above Equation, the Max HR represents the maximum heart rate and the Rest HR represents the lowest heart rate after an exercise starts.

The anaerobic threshold is 70 or more for a player, 50 to 60 for the general public, and 50 or less for the weakling.

An aerobic threshold (AeT) may be calculated as the following Equation 7.

Aerobic threshold (AeT)=0.5 (Max HR−Rest HR)+ Rest HR  [Equation 7]

A formula of basic metabolism in a nutritional treatment is calculated based on the following Equation 8.

Man: 66.47+(13.75×body weight)+(5×height)−(6.76× age)

Woman: 655.1+(9.56×body weight)+(1.85×height)− (4.68×age)  [Equation 8]

The in vivo nutrient content data may include at least one of moisture, carbon hydrate, protein, fat, an inorganic matter, an amount of vitamin that are included in a player's body as illustrated in the following Table 2.

TABLE 2

|  | Moisture (%) | Carbon hydrate (%) | Protein (%) | Fat (%) | Inorganic matter (%) | Vitamin (%) |
| --- | --- | --- | --- | --- | --- | --- |
| Optimal zone | 66 | 6 | 16 | 13 | 4 | 3 |
| Boundary zone | 61 | 3 | 13 | 10 | 3 | 2 |
| Risk zone | 56 | 0 | 10 | 7 | 2 | 1 |

Further, as illustrated in the following Table 3, the environmental element analysis data may include at least one of humidity of a stadium, temperature, wind volume, wind direction, altitude, and ground of a stadium, hardness and traction power of grass, an inclined ball rebound, a vertical ball rebound, ball rolling distance and speed, moisture of grass, a kind of grass, an elastic force, a pressure, and gravitational acceleration, a spinning rate, a non-spinning rate, a linear speed, a ground speed, and a post-bound speed of a ball, a size of a ball, a weight of a ball, and a repulsive force of a ball.

surrounding noise, fashions in each area, disease, anxiety information, taste, income and expenditure pattern, famine, and a war.

That is, the injury risk extraction unit 218 integrates the vital information of a player received from the guard 300, the environment information received from at least one external terminal 400, and the activity information of a player extracted from the game image received from the photographing unit 500 to index the vital analysis data, the in vivo nutrient content data, the environmental element analysis data, the operation analysis data, and the recording data of a player.

TABLE 4

|  | Living body/ position | In vivo nutrient content | Environment state analysis | Operation analysis | Recording analysis |
| --- | --- | --- | --- | --- | --- |
| Optimal zone | 100 | 100 | 100 | 100 | 100 |
| Boundary zone | 70 | 50 | 80 | 50 | 70 |
| Risk zone | 50 | 20 | 60 | 20 | 20 |

Further, the injury risk and the performance may be calculated by determining to which phase of the pre-stored normal, boundary and risk phases the indexed data correspond.

Further, the system 100 for managing a player may transmit the calculated injury risk to a player to allow the player to regulate his/her own condition for himself/herself or the calculated injury risk to the player conservancy terminal 600 carried by the player conservancy for managing a player or a judge, thereby preventing the injury of a player and smoothly progressing the game.

Figure 2:
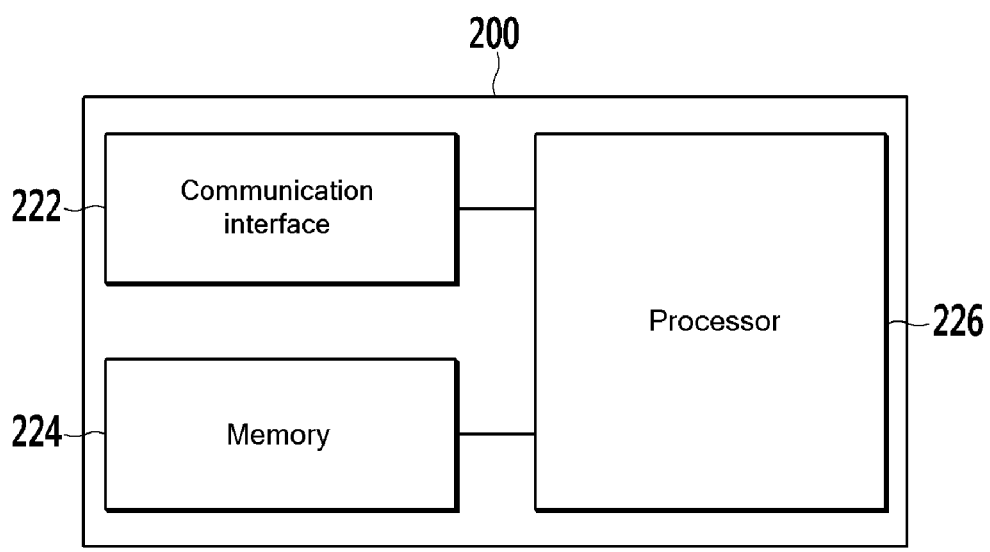
FIG. 2 is a hardware configuration diagram of an apparatus for managing a player according to an exemplary embodiment of the present invention.

FIG. 2 is a hardware configuration diagram of an apparatus for managing a player according to an exemplary embodiment of the present invention. The hardware configuration of the apparatus 200 for managing a player according to the exemplary embodiment of the present invention may be various according to a design. Referring to FIG. 2, the apparatus 200 for managing a player according

TABLE 3

|  | Temperature | Altitude | Ground | Hardness of grass | Traction force of grass | Inclined ball rebound of grass (1 m/45°) | Vertical ball rebound of grass (7 m /1.5 m) | Ball rolling distance and speed of grass | Moisture of grass | Kind of grass |
| --- | --- | --- | --- | --- | --- | --- | --- | --- | --- | --- |
| Optimal zone | 534 | 520 | 45 | 100 | 100 | 100 | 100 | 100 | 100 | 100 |
| Boundary zone | 438 | 2130 |  | 80 | 84 | 20 | 45 | 50 | 45 | 70 |
| Risk zone | 1142 | 231 |  |  |  |  |  |  |  |  |

|  | Elastic force | Pressure (lbs) | Gravitational acceleration | Spinning | Non- spinning | Linear speed | Ground speed | Post-bound speed | Size (cm) | Weight (g) | Repulsive force |
| --- | --- | --- | --- | --- | --- | --- | --- | --- | --- | --- | --- |
| Optimal zone | 100 | 11 | 100 | 100 | 100 | 100 | 100 | 100 | 68 | 45 | 100 |
| Risk zone | 70 | 0.9 | 30 | 30 | 10 | 75 | 50 | 30 | 70 | 41 | 70 |

Further, the operation analysis data may include at least one of a kick, a defense, an offense, shooting, heading, a pass, a good defense, ball trapping, ball dribble, a tackle, a throw in, a free kick, a corner kick, a foul, a score, a lost point, and a point of a player.

The recording data of a player may include at least one of a height, a weight, a food pattern, a sleep pattern, an injury, a disease record, drinking, and smoking of a player, support equipment, game importance, the number of fans, fan and to the exemplary embodiment of the present invention may include at least one communication interface 222, at least one memory 224, and a processor 226.

The communication interface 222 is hardware for physical connection to external devices. The communication interface 222 according to the exemplary embodiment of the present invention includes a wired/wireless communication interface for connection to the guard 300 carried by a player, at least one external terminal 400 holding various environment information that may affect a player, the photographing unit 500 photographing the game image and the player conservancy terminal 600.

The memory 224 is hardware for storing a variety of information required for the operation of the processor 226. The memory 224 may store an operating system (OS) for driving the processor 226 and programs for various operations of the apparatus 200 for managing a player described in the present invention.

The processor 226 communicates with the memory 224 and the communication interface 222 and controls them. The processor 110 may load the program stored in the memory 120 to integrate the vital information of a player, the activity information and the environment information to thereby accurately analyze a body condition and calculate the injury risk based on the pre-stored vital recovering ability data and transmit it to the player and the player conservancy.

FIG. 3A is a rear view of a guard in the system for managing a player according to the exemplary embodiment of the present invention, FIG. 3B is a front view of a guard in the system for managing a player according to the exemplary embodiment of the present invention, and FIG. 4 is a diagram illustrating a configuration of a sensing and alarm module of the guard according to the exemplary embodiment of the present invention.

Referring to FIG. 3A, the guard 300 is an apparatus worn at a player to protect a player from an external shock during a game and in the exemplary embodiment of the present invention, the guard 300 may be a shank guard worn at a soccer player's shank during a soccer game. However, the guard 300 is not necessarily limited thereto and therefore may be a permitted protective apparatus worn at various parts of a body according to regulations of various athletics.

Referring to FIGS. 3A and 3B, the guard 300 according to the exemplary embodiment of the present invention includes a main body part 302, shock absorption plastic 304, and a sensing and alarm module 306.

The main body part 302 easily discharges sweat and heat of a player and has a sponge material that may absorb a shock from the outside and the main body part 302 may be partially waterproofed to protect a terminal from moisture caused due to environmental factors such as sweat discharged from a player and rain. Referring to FIG. 3B, in the guard 300 according to the exemplary embodiment of the present invention, the outside of the main body part 302 may be further provided with the shock absorption plastic 304 that may bear the external shock. Further, the sensing and alarm module 306 is configured to acquire the vital information sensed from a player and be connected to the apparatus 200 for managing a player to alarm a player wearing the guard 300 of a risk signal and may penetrate the main body part 302 to be disposed in the main body part 302.

Referring to FIG. 4, the sensing and alarm module 306 in the main body part 302 includes a sensor unit 310 that may acquire vital information of a player, a communication unit 320, a risk signal alarm unit 330, a control unit 340, and a power unit 350.

The sensor unit 310 includes a sensor for collecting vital information of a player wearing the guard 300.

The vital information means information for understanding a body condition of a player wearing the guard 300 and may include at least one of, for example, a blood pressure, a blood flow, a heart rate, electrocardiogram, sweat, in vitro secretion, body temperature, an in vivo nutrient, a total body fluid, a muscle contraction, a nerve, and a ligament. The sensor unit 310 may include various kinds of sensors that may collect the vital information. For example, the sensor unit 310 may include at least one of a piezoelectric sensor measuring a pressure generated by a blood vessel expansion to collect blood pressure information, a photo sensor collecting a blood flow and a heart rate, an electrocardiogram (ECG) sensor collecting a waveform depending on a normal motion of a heart, a temperature sensor for collecting body temperature of a player, and various kinds of bio sensors collecting in vivo oxygen saturation of a player, sweat, lactic acid, a respiration volume, in vivo nutrient information of a player, moisture content information, muscle information, nerve information, and a ligament or pain condition.

In the guard 300 according to the exemplary embodiment of the present invention, the sensor unit 310 is positioned near a tibia artery and a tibia vein that are at each of the left and right shanks of a wearer. Further, the sensor unit 310 may be fixed in a band form to adhere to a sensing part and a skin to thereby acquire vital data from a nerve and a muscle of an anterior tibia artery part, thereby accurately sensing the vital information even at shanks far away from a heart. Further, in the guard according to the exemplary embodiment of the present invention, the sensor unit 310 may be provided with a plurality of sensors that are arranged in an array form to increase sensing accuracy. Therefore, even though the position of the guard 300 is changed depending on a player's motion during a game, it is possible to acquire the accurate sensing information by sensing the vital information from the plurality of sensors.

For example, in the exemplary embodiment of the present invention, the sensor unit 310 may be configured as the photo sensor. A light emitting unit of the photo sensor irradiates infrared rays toward a blood vessel of a wearer and a light receiving unit collects a light quantity reflected from a blood vessel to measure a change in blood flow of a wearer. In this case, when the sensor unit includes the photo sensors arranged in the array form to irradiate light to a blood vessel and collects the reflected light to measure the change in blood flow, if at least one of the plurality of photo sensors accurately corresponds to the blood vessel, the change in blood flow may be sensed by using the photo sensor accurately corresponding to the blood vessel even when other photo sensors are not positioned to accurately correspond to the blood vessel.

The communication unit 320 transmits the vital information of a player acquired by the sensor unit 310 to the apparatus 200 for managing a player and receives the risk information of a player from the apparatus 200 for managing a player. The communication unit 320 may be implemented as a radar, WIFI, LTE, and a radio frequency communication module that perform wireless communication using a predetermined frequency range.

Further, the communication unit 320 may wirelessly transmit in real time vital information of a wearer to an external medical staff, a rehabilitation trainer, a physical trainer, a couch, and a club managing a body condition of a player as well as the apparatus 200 for managing a player and even to viewers through broadcasting communication media.

When the communication unit 320 receives the risk information of a player from the apparatus 200 for managing a player, the risk signal alarm unit 330 may alarm a player of a risk situation in real time. In this case, as illustrated in FIG. 3B, the risk signal alarm unit 330 may be configured to allow a judge and a game insider to monitor a player's condition using a visual means such as a display unit 331 including at least one of an LED and a display However, the risk signal alarm unit 330 is not necessarily limited thereto and therefore the risk signal alarm unit 330 includes a speaker module to transmit a risk situation to a player using an auditory means. Alternatively, to strategically transmit the risk information only to a player wearing the guard 300 not to expose the risk information of a player to the other party in a strategy of a game operation, the risk signal alarm unit 330 may include a vibration module 332 to alarm a player of the risk situation using a vibration signal at a predetermined interval. That is, the risk signal alarm unit 330 may also be configured to allow a player to check his/her own condition for himself/herself.

The control unit 340 may correct the vital information acquired by the sensor unit 310 and perform a control to transmit the corrected vital information to the communication unit 320 and then the apparatus 200 for managing a player. Further, the control unit 340 may transmit the risk information of a player received from the communication unit 320 to the risk signal alarm unit 330 to transmit a risk situation to a player.

The control unit 340 may remove noise of the vital information acquired by the sensor unit 310. Further, the control unit 340 may also integrate the vital information measured by the left guard 300 and the vital information measured by the right guard 300. In this case, when it is determined that the accurate sensing is not performed by analyzing the acquired vital information, the sensing accuracy may be more improved by changing measurement parameters such as changing a measurement wavelength band of the sensor unit 310 and changing a measurement time, or the like.

According to the exemplary embodiment of the present invention, the control unit 340 may be implemented as a central processing unit (CPU) operating the whole of the guard 300 and may also include a data processing apparatus for converting a vital information measured by the sensor unit 310 into information that may be transmitted by the communication unit 320.

Further, the control unit 340 may determine that a player does not move or determine that a player does not wear the guard 300 based on the vital information acquired by the sensor unit 310 or stop various operations of the guard 300 when receiving a signal controlling the operation of the guard 300 from the outside through the communication unit 320, thereby preventing power from being unnecessarily consumed.

The power unit 350 is configured to supply power required to implement various operations of the sensor unit 310, the communication unit 320, the risk signal alarm unit 330, and the control unit 340 of the guard 300 and may be implemented as a small battery which may be sustained for at least 5 hours. The power unit 350 is a chargeable battery and may be charged by external power. In this case, the guard 300 according to the exemplary embodiment of the present invention may further include a power supply unit 352 including a charging terminal.

Although not illustrated in the drawings, the guard 300 of the system for managing a player according to the exemplary embodiment of the present invention may further include a camera that may photograph a player's motion. The camera may photograph a game image and transmit the photographed game image to the outside through the communication unit 320, thereby more realistically transmitting a game progress scene of players. Further, the camera may also be used to read a video.

As such, the guard 300 of the system for managing a player according to the exemplary embodiment of the present invention includes the main body part 302 having the sponge material performing a waterproof function and a sweat and heat discharge function and may adhere to a player's skin to acquire the vital information without giving any inconvenience to a player even though a wearer wears the guard 300 since the sensor unit 310 for acquiring the vital information and the risk signal alarm unit 330 are attached to the main body part 302. Further, the sensor unit 310 may be positioned near a tibia artery and a tibia vein that are at each of the left and right shanks of a wearer and is fixed in a band form to adhere to the sensing part to thereby acquire vital data from a nerve and a muscle of the anterior tibia artery part, thereby accurately acquiring the vital information of a player.

Figure 5:
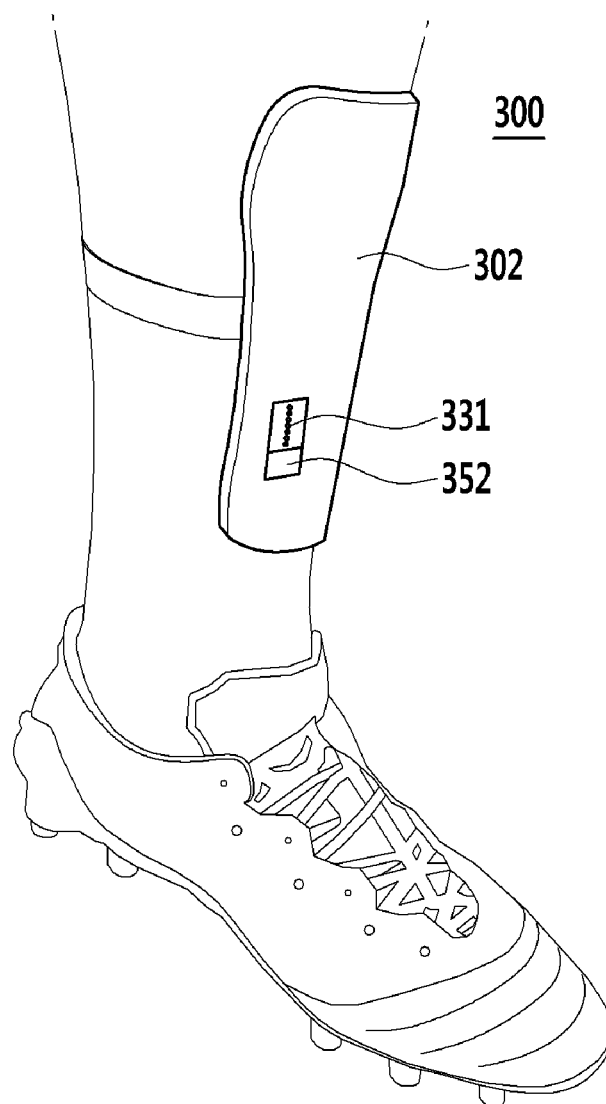
FIG. 5 is a diagram illustrating an example in which the guard according to the exemplary embodiment of the present invention is worn.
Figure 6:
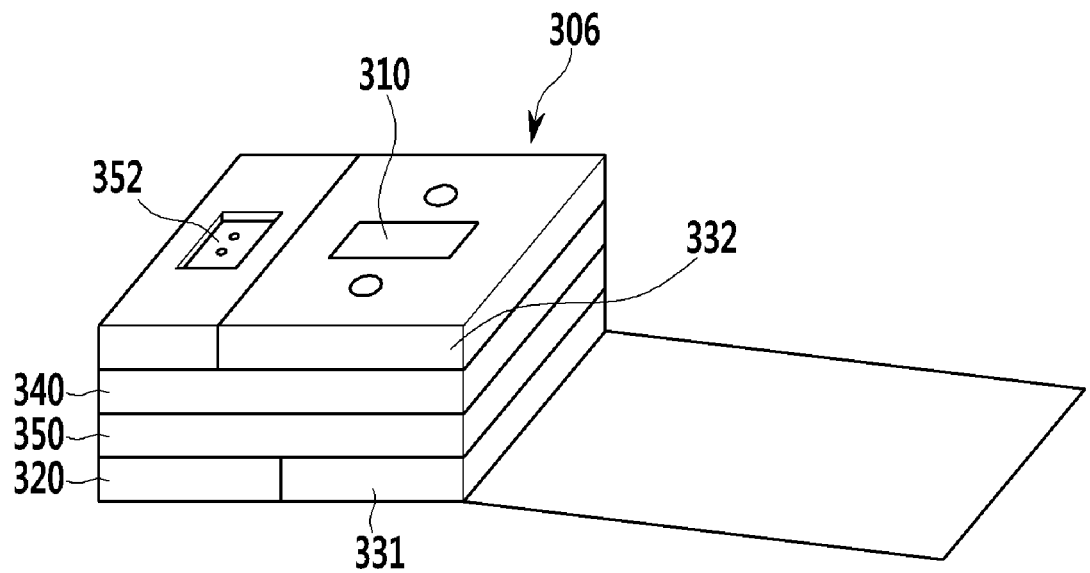
FIG. 6 is a perspective view of a sensing and alarm module of the guard according to the exemplary embodiment of the present invention.
Figure 7:
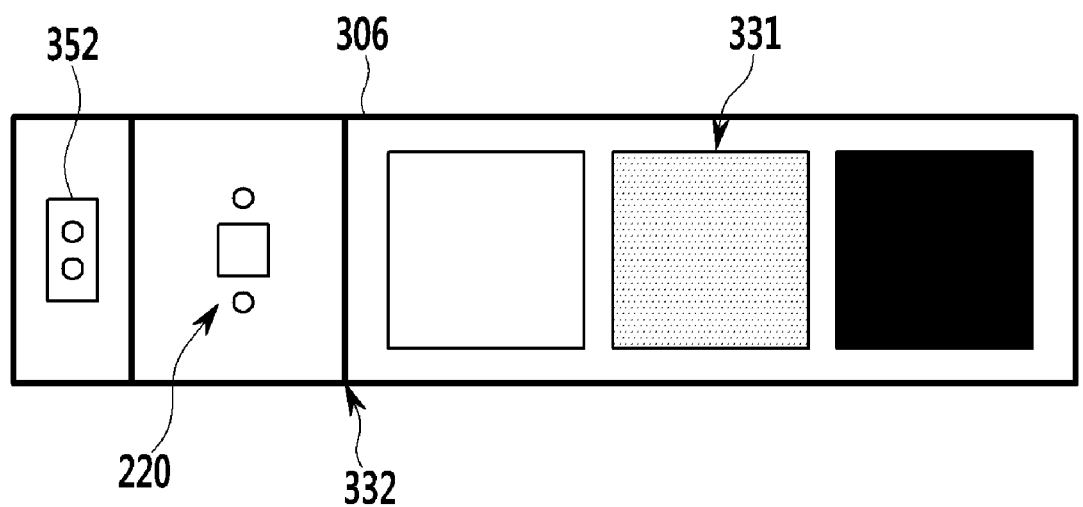
FIG. 7 is a plan view of the sensing and alarm module of the guard according to the exemplary embodiment of the present invention.

FIG. 5 is a diagram illustrating an example in which the guard according to the exemplary embodiment of the present invention is worn, FIG. 6 is a perspective view of a sensing and alarm module of the guard according to the exemplary embodiment of the present invention, and FIG. 7 is a plan view of the sensing and alarm module of the guard according to the exemplary embodiment of the present invention.

Referring to FIG. 5, the guard 300 according to the exemplary embodiment of the present invention may be worn at a shank part of a wearer. The guard 300 includes the main body part 302 and the sensing and alarm module 306 in the main body part 302.

The main body part 302 may easily absorb player's sweat and discharge heat and absorb a shock from the outside and may be partially waterproofed to protect a terminal from moisture caused by environmental factors such as sweat discharged from a player and rain.

The sensing and alarm module 306 is configured to acquire the vital information of a player, transmit the acquired vital information to the outside, and alarm a player and a game insider of the injury risk of a player received from the outside.

Referring to FIGS. 6 and 7, the sensing and alarm module 306 according to the exemplary embodiment of the present invention may include the sensor unit 310, the communication unit 320, the risk signal alarm unit 330, the control unit 340, and the power unit 350.

The sensing and alarm module 306 of the guard 300 according to the exemplary embodiment of the present invention has the sensor unit 310 and the power supply unit 352 disposed at an upper portion thereof contacting a player. The sensor unit 310 may adhere to the body part of the wearer to sense the vital information of the wearer. A lower portion of the sensor unit 310 is provided with the vibration module 332 for alarming a player of the risk information of a player using a vibration signal and a lower portion of the vibration module 332 is provided with the control unit 340 for controlling each function of the guard 300. A lower portion of the control unit 340 is provided with the power unit 350 for supplying power required to implement each function of the guard 300. A lower portion of the power unit 350 is provided with the communication unit 320 for performing communication with the outside and the display unit 331 for alarming the risk information of a player to the outside. The display unit 331 may be configured of three LEDs of red (R), green (G), and blue (B) to turn on other colors according to the injury risk of a player.

An upper end portion of the sensing and alarm module 306 having the above configuration may be inserted into the main body part 302 that is included in the guard 300 illustrated in FIG. 1. In this case, the sensor unit 310 sensing the vital information of a player and the vibration module 332 for alarming a player of a risk signal may adhere to a body of a wearer, for example, a shank part.

As illustrated in FIG. 6, the sensing and alarm module 306 of the guard according to the exemplary embodiment of the present invention may be formed in a stacked structure, which is only an example. Therefore, the sensor unit 310, the communication unit 320, the control unit 340, the risk signal alarm unit 330, and the power unit 350 that are included in the sensing and alarm module 306 according to the exemplary embodiment of the present invention may be variously disposed. Further, the sensor unit 310 may be designed in a band form to adhere to a skin, an anterior tibia artery, and various arteries, veins, and nerves and may be detachably changed and used.

Figure 8:
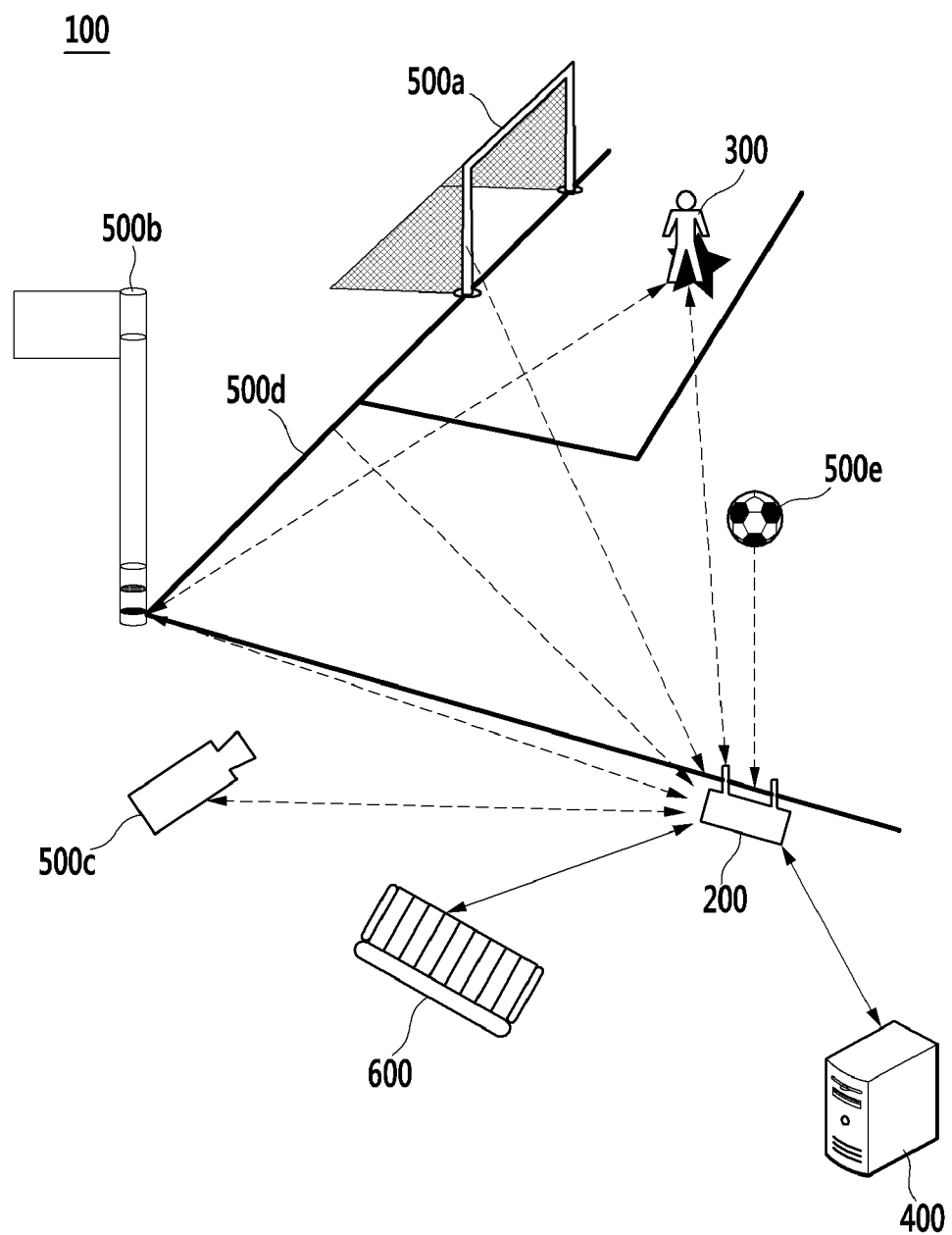
FIG. 8 is a diagram for describing the system for managing a player according to the exemplary embodiment of the present invention.

FIG. 8 is a diagram for describing the system for managing a player according to the exemplary embodiment of the present invention.

Referring to FIG. 8, the system 100 for managing a player according to the exemplary embodiment of the present invention includes the guard 300 which a player wears, the external terminal 400 transmitting player information and environment information within a stadium, a photographing unit 500 disposed in at least one of a ball, a goal post, a goal line, a relay camera, and a corner flag that are positioned within a stadium, the player conservancy terminal 600, and the apparatus 200 for managing a player that is connected to the guard 300, the external terminal 400, the photographing unit 500, and the player conservancy terminal 600.

First, the player participating in a soccer game wears the guard 300 and the sensing and alarm module 306 installed in the guard 300 may sense the vital information of a player using the sensor unit 310.

The vital information sensed by the sensor unit 310 may be transmitted to the apparatus 200 for managing a player through the communication unit 320. Alternatively, if it is determined that the vital information is an abnormal signal over a predetermined threshold value, the control unit 340 may directly alarm a wearer of a risk situation through the vibration module 332.

The apparatus 200 for managing a player receives the vital information of users from at least one guard 300 of a player.

The apparatus 200 for managing a player according to the exemplary embodiment of the present invention may scan and receive the environment information that may affect a physical and mental condition of a player from at least one external terminal 400. The environment information may include at least one of weather information of humidity, temperature, wind volume, wind direction, etc. within a stadium and stadium information of altitude, geological features, a grass state of a playground, etc.

Further, the apparatus 200 for managing a player may acquire the activity information including at least one of activity time, an activity distance, and activity mass of a player from an exercise sensor including an accelerator sensor or an angular sensor included in the guard 300 of a player. Alternatively, the game image may be obtained by photographing a player's motion by at least one photographing unit 500 disposed inside or outside a stadium and the player's motion may be sensed from the game image, thereby acquiring the activity information of a player, a position of players, and the environment information. The environment information may include at least one of the stadium and external environment information, that is, hardness of grass, a ground, moisture, a gravitational acceleration of a ball, a fan, temperature, altitude, wind, and movement of a ball The apparatus 200 for managing a player uses the received vital information, environment information, and activity information to calculate the injury risk of players depending on the vital recovering ability data of players stored in the vital recovering ability data storage unit 219. The vital recovering ability data may include at least one of data that may be generally applied according to a sex and an age of a player and an athletic event of a player and personal data that are measured during a game history and training that is already done by each player and individually accumulated.

Further, the apparatus 200 for managing a player may transmit the calculated injury risk to the guard 300 that a player wears and the player conservancy terminal 600 carried by the player conservancy. The player conservancy terminal 600 may be electronic devices such as a main computer, a tablet PC, and a smart phone.

Figure 9:
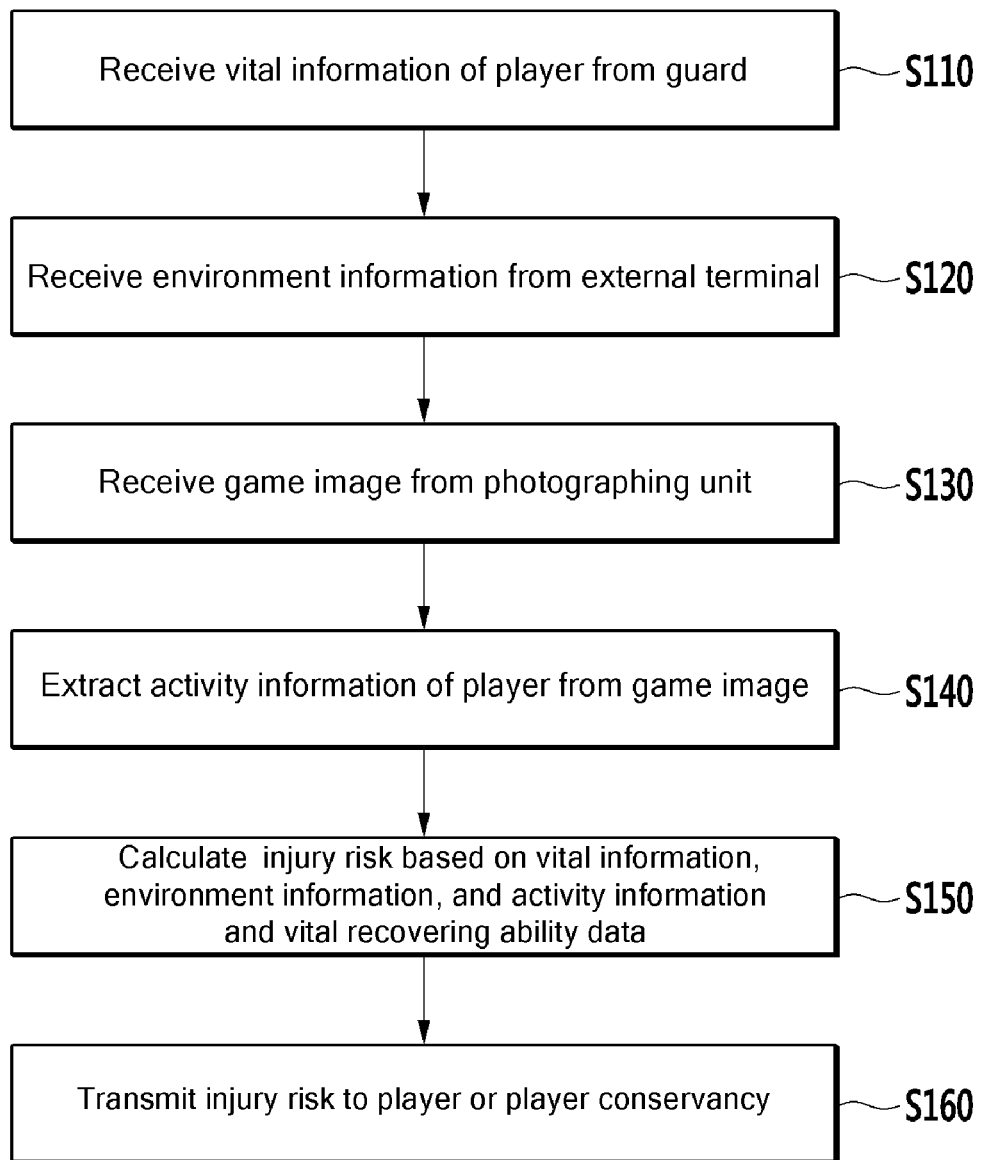
FIG. 9 is a flow chart of a method for managing a player with a guard by the apparatus for managing a player according to the exemplary embodiment of the present invention.

FIG. 9 is a flow chart of a method for managing a player with a guard by the apparatus for managing a player according to the exemplary embodiment of the present invention.

Referring to FIG. 9, the apparatus 200 for managing a player receives the vital information of a player from the guard 300 that a player wears (S110).

The guard 300 may include the sensor unit 310 for sensing a variety of vital information of a player and the communication unit 320 for transmitting the vital information and receiving the injury risk. The sensor unit 310 may include at least one of a piezoelectric sensor, a photo sensor, an electrocardiogram sensor, a temperature sensor, and a bio sensor for sensing the vital information of a player including at least one of a blood pressure, a blood flow, a heart rate, electrocardiogram, body temperature, sweat, in vitro secretion, in vivo nutrient, total body fluid, a muscle contraction, a nerve, a ligament, and pain information and may be configured as a plurality of sensor modules arranged in an array form to increase sensing sensitivity.

The apparatus 200 for managing a player receives the environment information from at least one external terminal 400 (S120).

The environment information means various kinds of information which may affect a physical and mental condition of a player. For example, the environment information may include at least one of weather information such as humidity, temperature, a wind volume, and a wind direction in a stadium and stadium information such as altitude, geological features, a grass state of a playground, and noise.

The apparatus 200 for managing a player receives the game image from the photographing unit 500 photographing the game image of a player (S130).

The photographing unit 500 may be disposed at a goal-post, a corner flag, and a line in a stadium or outside a stadium to relay a game to photograph a game image for monitoring a position of a player at various angles.

The apparatus 200 for managing a player uses the game image received from the photographing unit 500 to sense the position change of a player to thereby calculate the quantity of motion of players or monitors players' motions to extract the activity information of a player (S140).

Next, the apparatus 200 for managing a player integrates the vital information of a player received from the guard 300, the environment information received from at least one external terminal 400, and the activity information of a player extracted from the game image received from the photographing unit 500 to analyze the body condition of a player and calculates the injury risk on the basis of the vital recovering ability data (S150).

The vital recovering ability data may include at least one of data that may be generally applied according to a sex and an age of a player and an athletic event of a player and personal data that are measured during a game history and training that is already done by each player and individually accumulated.

Finally, the apparatus 200 for managing a player transmits the calculated injury risk to a player or a player conservancy (S160). Therefore, the player may receive the injury risk to control his/her own condition for himself/herself and the player conservancy may use an objective injury risk depending on the condition of a player to manage and protect the player.

The apparatus, system, and method for managing a player with a guard worn at a player according to an exemplary embodiment of the present invention may analyze the risk situations of players and alarm the players of the analyzed result to make the players regulate their pace for themselves, thereby predicting and preventing the injury to the players or the emergency accident.

The apparatus, system, and method for managing a player with a guard worn at a player according to an exemplary embodiment of the present invention may integrate the vital information that are acquired from the shank guard that the players wear, the exercise environment (altitude, humidity, temperature), and the vital activity data (maximum value and minimum value of the vital information of each player) of players, thereby accurately analyzing the risk degree of players.

Although the exemplary embodiment of the present invention has been described in detail hereinabove, the scope of the present invention is not limited thereto. That is, several modifications and alterations made by those skilled in the art using a basic concept of the present invention as defined in the claims fall within the scope of the present invention.

What is claimed is:

1. An apparatus for managing a player with a wearable guard including a sensor sensing vital information of the player and an operation and activity depending on a position of the player to calculate a warning sign and an injury risk of the player to thereby manage a condition of the player, the apparatus comprising:
   a communication interface configured to receive the vital information from the wearable guard and to transmit the warning sign and the injury risk to the wearable guard;
   a memory storing a program configured to calculate the warning sign and the injury risk to manage the condition of the player; and
   a processor connected to the communication interface and the memory and configured to execute an operation implemented by the program,
   wherein the communication interface is configured to receive environment information including at least one of humidity, temperature, a wind volume, a wind direction, altitude, latitude, geological features, a ground, and grass of a stadium, an inclined ball rebound, a vertical ball rebound, a ball rolling distance and speed, a size of grass, a moisture state of grass, a position, rotation, strength, an elastic force, a pressure, and a gravitational acceleration of a ball, spinning of the ball, a speed of the player and the ball, a bound, a straight, and a ground from an external terminal, and
   wherein the program includes instructions integrating the vital information, pre-stored vital recovering ability data of the player, and the environment information to calculate the injury risk of the player.

2. The apparatus of claim 1,
   wherein the vital information includes at least one of a blood flow, a heart rate, electrocardiogram, electromyogram, body temperature, lactic acid, sweat, in vitro secretion, respiration, oxygen saturation, moisture, in vivo nutrient, ligament elasticity, nerve reaction, pain information, an activity distance, activity time, an activity operation, and a position of the player, and
   wherein the program includes instructions using a variation of the vital information and the pre-stored vital recovering ability data to calculate the injury risk of the player.

3. The apparatus of claim 1,
   wherein the wearable guard comprises:
   a sensor configured to sense the vital information of the player;
   a communication unit configured to transmit the vital information and receive the injury risk from the apparatus; and
   a risk signal alarm to communicate the warning sign and the injury risk.

4. A method for managing a player with a wearable guard including a sensor sensing vital information of the player to allow an apparatus for managing a player to calculate an injury risk of the player to thereby manage a condition of the player, the method comprising:
   receiving the vital information from the wearable guard;
   receiving environment information including at least one of humidity, temperature, a wind volume, a wind direction, altitude, and geological features of a stadium, a grass state of the stadium, and a position and a motion of a ball from an external terminal;
   calculating the injury risk using pre-stored vital recovering ability data and the vital information; and
   transmitting the injury risk to the wearable guard,
   wherein in the calculating of the injury risk,
   the injury risk of the player is calculated by integrating the vital information, the pre-stored vital recovering ability data of the player, and the environment information.

5. The method of claim 4,
   wherein the vital information comprises at least one of a blood flow, a heart rate, electrocardiogram, electromyogram, body temperature, lactic acid, sweat, in vitro secretion, respiration, oxygen saturation, moisture, in vivo nutrient, ligament elasticity, nerve reaction, and pain information.

6. The method of claim 4, further comprising:
   transmitting the injury risk to a terminal of a coach or a medical staff monitoring the player.

7. A system for managing a condition of a player, the system comprising:
   a wearable guard configured to be worn by the player; and
   an apparatus configured to calculate an injury risk of the player,
   wherein the wearable guard comprises:
   a sensor configured to be attached to a body of the player to sense vital information of the player, wherein the apparatus comprises:
   a vital recovering ability data storage unit storing vital recovering ability data of the player;
   a vital information acquisition unit configured to receive the vital information of the player from the wearable guard;
   an environment information acquisition unit configured to receive environment information from at least one external terminal, the environment information including at least one of humidity, temperature, a wind volume, a wind direction, altitude, latitude, geological features, a ground, and grass of a stadium, an inclined ball rebound, a vertical ball rebound, a ball rolling distance and speed, a size of grass, a moisture state of grass, a position, rotation, strength, an elastic force, a pressure, and a gravitational acceleration of a ball, spinning of the ball, a speed of the player and the ball, a bound, a straight, and a ground from an external terminal; and an injury risk extraction unit configured to use the vital information, the environment information, and the vital recovering ability data to extract the injury risk of the player.

8. The system of claim 7,
wherein the apparatus further comprises:
a communication module configured to transmit the injury risk to the wearable guard of the player or a terminal of a coach or a medical staff monitoring the player.

* * * * *